United States Patent [19]

Kakimoto et al.

[11] Patent Number: 4,748,187

[45] Date of Patent: May 31, 1988

[54] OPIOID PEPTIDE-DEGRADING ENZYME INHIBITOR WITH A GERMANIUM COMPOUND

[75] Inventors: Norihiro Kakimoto; Takashi Katayama, both of Tokyo; Tadahiko Hazato, Saitama; Tsutomu Ohnishi, Tokyo, all of Japan

[73] Assignee: Asai Germanium Research Institute, Tokyo, Japan

[21] Appl. No.: 930,561

[22] Filed: Nov. 14, 1986

Related U.S. Application Data

[62] Division of Ser. No. 626,787, Jul. 2, 1984, Pat. No. 4,681,960.

[30] Foreign Application Priority Data

Jul. 1, 1983 [JP] Japan ............................ 58-119856
Jul. 11, 1983 [JP] Japan ............................ 58-125725

[51] Int. Cl.$^4$ ............................................. A61K 31/28
[52] U.S. Cl. .................................................. 514/492
[58] Field of Search ............................................ 514/492

[56] References Cited

U.S. PATENT DOCUMENTS 4,271,084 6/1981 Ishikawa et al. ............... 260/429 R
4,508,654 4/1985 Chang et al. ................... 260/429 R

FOREIGN PATENT DOCUMENTS 55-105696 8/1980 Japan .
57-203090 12/1982 Japan .

Primary Examiner—Stanley J. Friedman
Attorney, Agent, or Firm—Burns, Doane, Swecker & Mathis

[57] ABSTRACT

The present invention provides (1) a new organogermanium compound of the following general formula:

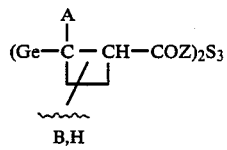

wherein A represents a hydrogen atom, a lower alkyl group such as a methyl or ethyl group or a phenyl group, B represents a hydrogen atom or a lower alkyl group as mentioned above and Z represents a hydroxyl or amino group and (2) an opioid peptide-degrading enzyme inhibitor containing the compound (1) as a principal ingredient.

11 Claims, No Drawings

OPIOID PEPTIDE-DEGRADING ENZYME INHIBITOR WITH A GERMANIUM COMPOUND

This application is a division of application Ser. No. 626,787, filed July 2, 1984, now U.S. Pat. No. 4,681,960.

BACKGROUND OF THE INVENTION

1. Field of the Invention

The present invention relates to organogermanium compounds having new structures and a strong opioid peptide-degrading enzyme inhibitor containing the same as a principal ingredient.

2. Description of the Prior Art

Germanium (Ge), known as a homologue of carbon, has semiconductive effect like silicon (Si) as a special property and, in addition, it has been studied in this aspect for a long time. Recently, the studies of organogermanium compounds have been advanced and the results thereof have been reported and they have attracted public attention in various technical fields.

It is well known from reports of numerous scientific meetings and literature that a carboxyethylgermanium sesquioxide $(GeCH_2CH_2COOH)_2O_3$, as a macromolecular compound (a propionic acid derivative of germanium) containing a 12-membered ring as a unit structure in which germanium atoms and oxygen atoms are arranged alternately, has quite excellent physiological effects such as strong hypotensive and antineoplastic effects, and it is free from toxicity or adverse reaction.

It has also been reported that when the above mentioned organogermanium compound is administered to a patient who complains of pain such as a cancerous pain, the growth of the tumor is inhibited and the dose of a narcotic analgesic such as morphine required for relieving the pain can be reduced. For this fact, the following hypothesis has been given.

Namely, when morphine or the like is administered, peptides generally called "opioid peptides" are liberated in vivo. This opioid peptide and morphine share the same receptor to control the autoanalgesic activity in vivo. A reason why the dose of morphine or the like can be reduced by the administration of the organogermanium compound is that the organogermanium compound inhibits the action of opioid peptide-degrading enzyme which inactivate the opioid peptide by decomposition in vivo to improve the efficiency of the opioid peptide in vivo.

However, the mechanism of the physiological activity of the organogermanium compound has not fully been known. As for the antineoplastic effects, some researchers reported that the effect is realized based on a germanium-oxygen bond in the structure. If an organogermanium compound containing an analogous atom in place of the oxygen atom can be synthesized, the use of the resulting compound for a purpose different from that of the known organogermanium compound can be expected.

SUMMARY OF THE INVENTION

The present invention has been completed under these circumstances. It is an object of the present invention to provide organogermanium compounds having the following general formula:

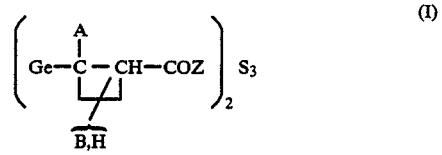

wherein A represents a hydrogen atom, a lower alkyl group such as a methyl or ethyl group or a phenyl group, B represents a hydrogen atom or a lower alkyl group as mentioned above and Z represents a hydroxyl or amino group.

Another object of the present invention is to provide an opioid peptide-degrading enzyme inhibitor which comprises as a principal ingredient an organogermanium compound of the following general formula:

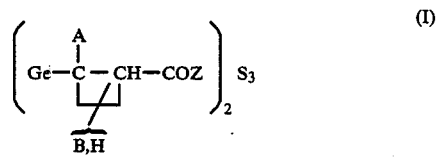

wherin A represents a hydrogen atom, a lower alkyl group such as a methyl or ethyl group or phenyl group, B represents a hydrogen atom or a lower alkyl group as mentioned above and Z represents a hydroxyl or amino group.

DETAILED DESCRIPTION OF THE PREFERRED EMBODIMENTS

In the organogermanium compound of the present invention, a germanium atom is bonded with propionic acid derivative (when Z is OH) or its amide (when Z is $NH_2$), in which a substituent A is placed in an $\alpha$-position and substituent(s) B is (are) placed in $\alpha$-position and/or $\beta$-position to the germanium atom on this propionic acid skeleton to form a germylpropionic acid as a base construction (in which carbon atoms on the propionic acid skeleton not bonded with the substituent B are bonded with hydrogen atoms), and germanium atoms of this base construction and the sulfur atoms are bonded in a ratio of 2/3 to form a ethylgermanium sesquisulfide.

The substituent A is a hydrogen atom, a lower alkyl group such as a methyl, ethyl or propyl group or a substituted or unsubstituted phenyl group. The substituent B is a hydrogen atom or an alkyl group as mentioned in the substituent A. Therefore, the organogermanium compounds of the present invention include the following compounds:

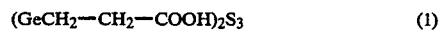

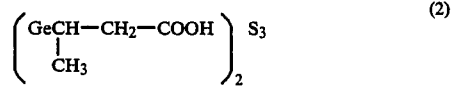

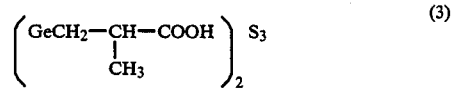

-continued (4) $\left\{ \begin{array}{c} \text{CH}_3 \\ | \\ \text{Ge}-\text{CH}-\text{CH}-\text{COOH} \\ | \\ \text{CH}_3 \end{array} \right\}_2 S_3$ (5) $\left\{ \begin{array}{c} \text{CH}_3 \\ | \\ \text{Ge}-\overset{|}{\text{C}}-\text{CH}_2-\text{COOH} \\ | \\ \text{CH}_3 \end{array} \right\}_2 S_3$ (6) $\left\{ \text{Ge}-\text{CH}-\text{CH}_2-\text{COOH} \right\}_2 S_3$ (with phenyl group on CH)

(7) $\left\{ \text{Ge}-\text{CH}-\text{CH}-\text{COOH} \atop \text{CH}_3 \right\}_2 S_3$ (with phenyl group on first CH)

(8) $(\text{GeCH}_2-\text{CH}_2-\text{CONH}_2)_2 S_3$ (9) $\left( \begin{array}{c} \text{GeCH}-\text{CH}_2-\text{CONH}_2 \\ | \\ \text{CH}_3 \end{array} \right)_2 S_3$

(10) $\left( \begin{array}{c} \text{GeCH}_2-\text{CH}-\text{CONH}_2 \\ | \\ \text{CH}_3 \end{array} \right)_2 S_3$

(11) $\left\{ \begin{array}{c} \text{CH}_3 \\ | \\ \text{Ge}-\text{CH}-\text{CH}-\text{CONH}_2 \\ | \\ \text{CH}_3 \end{array} \right\}_2 S_3$

(12) $\left\{ \begin{array}{c} \text{CH}_3 \\ | \\ \text{Ge}-\overset{|}{\text{C}}-\text{CH}_2-\text{CONH}_2 \\ | \\ \text{CH}_3 \end{array} \right\}_2 S_3$

(13) $\left\{ \text{Ge}-\text{CH}-\text{CH}_2-\text{CONH}_2 \right\}_2 S_3$ (with phenyl group)

(14) $\left\{ \text{Ge}-\text{CH}-\text{CH}-\text{CONH}_2 \atop \text{CH}_3 \right\}_2 S_3$ (with phenyl group)

The compounds in the present invention are represented as above, since the ratio of the germylpropionic acid to the sulfur atom is 2/3 in these compounds. The compounds of the present invention may be represented also as follows:

$$\left\{ \text{Ge}-\overset{A}{\underset{\widehat{B,H}}{\text{C}}}-\text{CH}-\text{COZ} \right\}_{2n} S_{3n}$$

or $$\left[ \left\{ \text{Ge}-\overset{A}{\underset{\widehat{B,H}}{\text{C}}}-\text{CH}-\text{COZ} \right\}_2 S_3 \right]_n$$

The compounds of the present invention having the above mentioned structures may be prepared by various processes.

The compounds of the general formula (I) wherein Z represents OH [i.e. compounds (I')] may be prepared by reacting a corresponding trichlorogermanium compound (II) with dry hydrogen sulfide gas (H$_2$S) in the presence of a base such as pyridine in an organic solvent as shown by the following reaction scheme (I):

Reaction scheme (1)

$$\text{Cl}_3\text{Ge}-\overset{A}{\underset{\widehat{B,H}}{\text{C}}}-\text{CH}-\text{COOH} \xrightarrow[\text{base}]{\text{H}_2\text{S}} \left( \text{Ge}-\overset{A}{\underset{\widehat{B,H}}{\text{C}}}-\text{CH}-\text{COOH} \right)_2 S_3$$

II    I'

The compounds of the general formula (I) wherein Z is NH$_2$ [i.e. compounds (I'')] may be prepared by first converting the same trichlorogermanium compound (II) as above into a corresponding acid chloride (III), then reacting the same with ammonia (NH$_3$) to form an amide (IV) and reacting the product with dry hydrogen sulfide gas in the presence of a base in an organic solvent in the same manner as above, as shown by the following reaction scheme (2):

Reaction scheme (2)

$$(\text{II}) \xrightarrow{\text{chlorinating agent}} \text{Cl}_3\text{Ge}-\overset{A}{\underset{\widehat{B,H}}{\text{C}}}-\text{CH}-\text{COCl} \xrightarrow{\text{NH}_3}$$

III $$\text{Cl}_3\text{Ge}-\overset{A}{\underset{\widehat{B,H}}{\text{C}}}-\text{CH}-\text{CONH}_2 \xrightarrow[\text{base}]{\text{H}_2\text{S}} \left( \text{Ge}-\overset{A}{\underset{\widehat{B,H}}{\text{C}}}-\text{CH}-\text{CONH}_2 \right)_2 S_3$$

IV    I''

In the above reaction scheme (1) and (2), a mercapto compound of the formula:

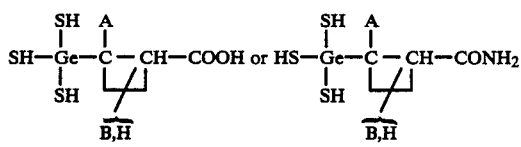

is formed by the reaction with hydrogen sulfide. This mercapto compound may be either isolated or not. When this compound is isoloated, intermolecular hydrogen sulfide elimination occurs to form a structure of the general formula (I).

The trichlorogermanium compound (II) being used in the above mentioned reaction may be prepared by a process disclosed in the specification of Japanese Patent Publication No. 2964/1971 as follows:

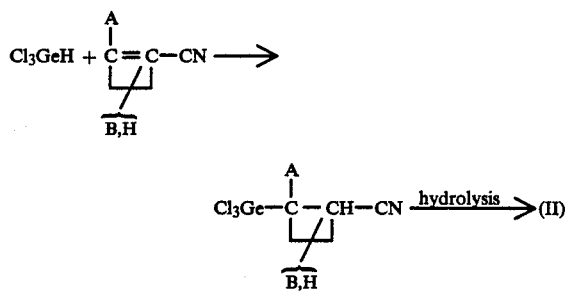

Alternatively, the compound (II) may be prepared by directly reacting the same starting material as above with an acrylic acid derivative as follows:

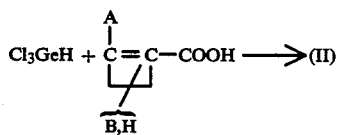

The thus-obtained compounds of the present invention including the above mentioned compounds (1) to (14) are colorless, transparent crystals having a melting poing (or decomposition point) of generally around 200° C. The results of elementary analyses coincide with values calculated from the respective molecular formulae, differences between them being within the range of measuremental error. The results of infrared (IR) absorption spectrum and nuclear magnetic resonance (NMR) absorption spectrum prove that the compounds of the present invention are those shown by the above general formula (I).

The compounds of the present invention are characterized in that they are slightly soluble in water and highly soluble in an organic solvent miscible with water, such as acetone or alcohol, namely they are oil-soluble, while the above mentioned carboxyethylgermanium sesquioxide is slightly soluble in water and insoluble in an organic solvent at all.

The organogermanium compounds of the present invention have the germanium-sulfur bonds very close to the germanium-oxygen bonds in the known carboxyethylgermanium sesquioxide. It is expected, therefore, when the compound of the present invention is administered to a living body, similar antineoplastic effect, etc., are obtained. In this connection, it is to be noted that the effect of the organogermanium compounds of the present invention resides in a strong inhibition of the opioid peptide-degrading actions of the above mentioned opioid peptide-degrading enzyme.

Namely, as described above, the substances generally called "opioid peptides" which are peptides found in the living bodies are quite important compounds managing the autoanalgesic activity in vivo. The opioid peptides includes several compounds such as enkephalin isolated from swine or bovine brains by Hughes et al. in 1975 and having the following structure:

$H_2N$-Tyr-GlY-Gly-Phe-Met-OH

As the enzymes which degrade the opioid peptides such as enkephalin, there have been found numerous enzymes such as dipeptidylaminopeptidase and aminopeptidase which can be separated from various living tissues and purified. It has been found that when these enzymes are reacted on the opioid peptides or their model compounds in the presence of the compound of the present invention, the compound of the invention strongly inhibit the action of the enzymes.

The effects of the compounds of the present invention are quite strong. For example, the compound (4) has 97.0% inhibition against the effect of aminopeptidase (derived from bovine longitudinal muscle) on enkephalin, i.e. one of the opioid peptide. Thus, when an opioid peptide-degrading enzyme inhibitor in the form of a solid preparation such as tablets, powder, granules or capsules or a liquid preparation such as an injection, containing the organogermanium compound of the present invention as the principal ingredient is administered to a living body, the effects of the opioid peptide-degrading enzyme is remarkably inhibited and the effective utilization of the opioid peptide is improved. Consequently, the medical effects of a narcotic substance such as morphine become remarkable and the dose of the narcotic substance to be used for obtaining a given medical effect can be reduced. Thus, side effects brought about by the continuous use of the narcotic substance such as habituation and addiction can be relieved.

Dipeptidylcarboxypeptidase which is one of the opioid peptide-degrading enzymes acts also as an converting enzyme for angiotensin I which is a precursor of angiotensin II (an enzyme having a quite strong hypertensive effect). Therefore, when this effect of the enzyme is inhibited, the inhibitor also acts on a renin/angiotensin/aldosterone system to exert preferred influences on the living body, particularly blood pressure maintenance mechanism.

The following examples will further illustrate the present invention.

EXAMPLE 1

Preparation of compound (I') of the present invention

Synthesis of compound (1)

25.2 g (0.1 mol) of β-trichlorogermylpropionic acid was dissolved in 200 ml of anhydrous benzene. 24 g (0.1 mol) of anhydrous pyridine was added to the solution and the mixture was stirred. Then, dry hydrogen sulfide gas was introduced therein for 60 min. Benzene was removed carefully from the resulting oily product and then the residue was dissolved in 100 ml of methanol. The solution was added to 300 ml of purified water and crystals thus formed were recrystallized from methanol to obtain 16.2 g of compound (1) of the present invention in the form of colorless plate. Yield was 78%.

Compound (1)

melting point: 200° C. (calcutated from the DTA spectrum; the same shall apply hereinafter)

| | elementary analysis: | | | |
|---|---|---|---|---|
| | Ge | C | H | S |
| found | 37.44 | 18.61 | 2.62 | 24.83 |
| calculated | 37.41 | 18.58 | 2.62 | 24.88 |

IR (KBr, cm$^{-1}$) 3420, 1710, 425

NMR (methanol d$_4$ σ) 1.97 (2H, t, Ge—C$\underline{H}_2$), 2.67 (2H, t, C$\underline{H}_2$—CO)

Synthesis of compound (4)

20.02 g (0.2 mol) of (E)-2-methyl-2-butenoic acid was dissolved in 100 ml of dry ethyl ether. 36.0 g (0.2 mol) of trichlorogermane was added to the solution and stirred for 2 hrs. Crystals thus formed were recrystalized from n-hexane to obtain 42.86 g (yield: 76.5%) of 2-methyl-3-(trichlorogermyl)butanoic acid in the form of colorless plate.

Then, 5.6 g (0.02 mol) of 2-methyl-3-(trichlorogermyl)-butanoic acid prepared as above was dissolved in 100 ml of anhydrous benzene. 5.2 g (0.066 mol) of anhydrous pyridine was added to the solution and the mixture was stirred and dry hydrogen sulfide gas was introduced therein for 60 min. A compound thus precipitated was separated and then recrystallized from anhydrous acetone or purified by isolating the same by means of a molecular sieve such as Sephadex LH-20 (trade name) using methanol as a eluant to obtain 3.2 g of compound (4) of the present invention. Yield was 72.1%.

Compound (4)

melting point: 235° C.

| | elementary analysis: | | | |
|---|---|---|---|---|
| | Ge | C | H | S |
| calculated: | 32.73 | 27.07 | 4.09 | 21.68 |
| found: | 32.50 | 27.13 | 4.02 | 21.92 |

IR (KBr, cm$^{-1}$) 3400, 2960, 1700, 1445, 1225, 820, 680, 600, 425

NMR (CD$_3$OD, σ) 1.33 (3H, dd, Ge—CH—CH$_3$), 1.40 (3H, dd, CO—CH—CH$_3$), 2.18 (1H, m, Ge—C$\underline{H}$), 2.80 (1H, m, CO—C$\underline{H}$)

Other compounds may also be prepared in the same manner as above. The physical properties of the compounds (I') are shown in Tabel (1).

EXAMPLE 2

Preparation of compound (I'') of the present invention

Synthesis of compound (11)

28.0 g (0.1 mol) of 2-methyl-3-(trichlorogermyl)-butanoic acid was treated with 100 ml of thionyl chloride and then distilled under reduced pressure to obtain 27.0 g (yield: 90.4%) of 2-methyl-3-(trichlorogermyl)-butanoyl chloride as a light yellow fraction having a boiling point of 99° to 100° C./6 mmHg.

5.8 g (0.02 mol) of this chloride was dissolved in 50 ml of anhydrous benzene. Dry ammonia was introduced therein under cooling with ice for 1 h. Then, dry hydrogen chloride gas was introduced therein for 1 h. 100 ml of methyl acetate was added thereto and the mixture was stirred and filtered. The filtrate was distilled and the residue was recrystallized from a liquid mixture of acetone/benzene (1/2) to obtain 4.1 g (yield: 76.0%) of 2-methyl-3-(trichlorogermyl)butanamide.

10.8 g (0.04 mol) of the obtained 2-methyl-3-(trichlorogermyl)butanamide was dissolved in 200 ml of anhydrous benzene. 9.5 g (0.12 mol) of anhydrous pyridine was added to the solution and the mixture was stirred. Dry hydrogen sulfide gas was introduced therein for 60 min. A compound thus precipitated was separated and then recrystallized from anhydrous acetone or purified by isolating the same by means of a molecular sieve such as Sephadex LH-20 (trade name) using methanol as a eluant to obtain 7.8 g of compound (11) of the present invention. Yield was 88.3%.

Compound (11)

melting point: 205° C. (decomposition)

| | elementary analysis: | | | | |
|---|---|---|---|---|---|
| | Ge | C | H | N | S |
| calculated: | 32.87 | 27.20 | 4.56 | 6.34 | 21.87 |
| found: | 32.59 | 27.37 | 4.43 | 6.25 | 21.56 |

IR (KBr, cm$^{-1}$) 3400, 3200, 2960, 1660, 1460, 1400, 780, 570, 420

NMR (CD$_3$OD, σ) 1.30 (3H, d, Ge—CH—CH$_3$), 1.38 (3H, d, CO—CH—CH$_3$), 2.14 (1H, m, Ge—C$\underline{H}$), 2.71 (1H, m, CO—C$\underline{H}$), Other compounds were prepared in the same manner as above. The physical properties of the compounds (I'') are shown in Table (2).

TABLE (1)

| Compound | Elementary analysis calculated/found | | | | Melting point | IR(KBr, cm$^{-1}$) | (Solvent) | NMR (δ) | Yield (%) |
|---|---|---|---|---|---|---|---|---|---|
| | Ge | C | H | S | | | | | |
| (2) | 34.91 / 34.87 | 23.13 / 23.18 | 3.40 / 3.43 | 23.15 / 23.24 | 185 (dec) | 3420, 1705, 425 | CD$_3$OD | 1.36(3H, d, C$\underline{H}_3$) 2.08~2.95 (3H, m, C$\underline{H}$, C$\underline{H}_2$) | 57.7 |
| (3) | 34.91 / 34.95 | 23.13 / 23.17 | 3.40 / 3.47 | 23.15 / 23.09 | 196 (dec) | 3410, 1705, 425 | CD$_3$OD | 1.38(3H, d, —C$\underline{H}_3$) 2.03(2H, m, —C$\underline{H}_2$—) 2.94(1H, m, —CH—) | 93 |
| (5) | 32.73 / 32.44 | 27.07 / 27.00 | 4.09 / 4.16 | 21.68 / 21.74 | 205 (dec) | 3450, 2960, 1700, 1460, 1380, 1220, 1130, 680, 620, 425 | CD$_3$OD | 1.46(6H, s, ─C$\underline{H}_3$)$_2$), 2.60(2H, s, —C$\underline{H}_2$) | 80.3 |

TABLE (1)-continued

| Com-pound | Elementary analysis Ge | C | calculated found H | S | Melting point | Physical Properties IR(KBr, cm$^{-1}$) | (Solvent) | NMR (δ) | Yield (%) |
|---|---|---|---|---|---|---|---|---|---|
| (6) | 26.90 / 26.41 | 40.06 / 40.32 | 3.36 / 3.54 | 17.82 / 17.82 | 265 (dec) | 3450, 3040, 2850, 1710, 1600 1410, 1230, 700, 425 | CD$_3$OD | 3.00(2H, d, C$\underline{H}_2$CO), 3.55(1H, t, Ge—C$\underline{H}$—), 7.25(5H, m, —C$_6$$\underline{H}_5$) | 94.1 |
| (7) | 25.57 / 25.68 | 42.31 / 42.22 | 3.91 / 4.03 | 16.94 / 16.99 | 215 (dec) | 3450, 3030, 2980, 1705, 1455 1210, 820, 700, 680, 420 | CD$_3$OD | 1.43(3H, d, —C$\underline{H}_3$), 3.27(2H, m, —C$\underline{H}$—C$\underline{H}$—), 7.17(5H, m, —C$_6$$\underline{H}_5$) | 86.0 |

TABLE (2)

| Com-pound | Elementary analysis Ge | C | calculated found H | N | S | Melting point | IR(KBr, cm$^{-1}$) | (solvent) | NMR (δ) | Yield (%) |
|---|---|---|---|---|---|---|---|---|---|---|
| (8) | 37.63 / 38.00 | 18.70 / 18.77 | 3.14 / 3.12 | 7.27 / 7.18 | 24.96 / 24.96 | 225~226 (dec) | 3340, 1665, 1620, 1200 1400, 425 | DMF—d$_7$ | 1.98(2H, t, Ge—C$\underline{H}_2$) 2.56(2H, t, CO—C$\underline{H}_2$) | 60.2 |
| (9) | 35.07 / 35.11 | 23.24 / 23.31 | 3.90 / 4.00 | 6.78 / 6.69 | 23.27 / 23.31 | 248 (dec) | 3300, 3200, 1600, 1400 430 | CD$_3$OD | 1.33(3H, d, Ge—CH—C$\underline{H}_2$) 2.17~2.77 (3H, m, Ge—C$\underline{H}$—CH$_2$) | 84.1 |
| (10) | 35.07 / 35.41 | 23.24 / 23.42 | 3.90 / 3.92 | 6.78 / 6.53 | 23.27 / 23.23 | 225 (dec) | 3300, 3200, 1660, 1460 1400, 430 | CD$_3$OD | 1.23(3H, d, —C$\underline{H}_3$) 1.67~2.25 (3H, m, Ge—C$\underline{H}$—CH$_2$) | 83.2 |
| (12) | 32.87 / 32.96 | 27.20 / 27.14 | 4.56 / 4.68 | 6.34 / 6.11 | 21.78 / 21.53 | 230 (dec) | 3400, 3200, 2960, 1660, 1460 1120, 420 | CD$_3$OD | 1.22(6H, s, C$\underline{H}_3$—C—C$\underline{H}_3$) 2.60(2H, s, —C$\underline{H}_2$—CO) | 76.5 |
| (13) | 27.00 / 27.26 | 40.20 / 40.34 | 3.75 / 3.93 | 5.21 / 5.18 | 17.89 / 17.66 | 210 (dec) | 3450, 3350, 3200, 1660, 1600 1400, 765, 700, 420 | CD$_3$OD | 2.90(2H, m, —C$\underline{H}_2$—) 3.55(1H, m, C$\underline{H}$—) 7.19(5H, s, -$_6\underline{H}_5$) | 81.8 |
| (14) | 25.66 / 25.87 | 42.46 / 42.49 | 4.27 / 4.33 | 4.95 / 4.70 | 17.00 / 16.86 | 215 (dec) | 3450, 3350, 3200, 1660, 1455 1400, 700, 420 | CD$_3$OD | 1.42(3H, m, —C$\underline{H}_3$) 3.23(2H, m, —C$\underline{H}$—C$\underline{H}$—) 7.15(5H, S, —C$_6$$\underline{H}_5$) | 82.3 |

EXAMPLE 3

Pharmacological effects of the compound of the present invention (1) As described above, the inhibitor of the present invention has a strong effect of inhibiting the action of the opioid peptide-degrading enzyme. However, it is difficult to prove the effects of the products of the present invention unlike other general medicines, since problems are posed because the number of cases in which narcotic drugs are used for the treatment of diseases is not so large and the conditions of the patients in these cases are serious generally. On the other hand, however, some opioid peptides released in vivo when such narcotic substances are given and opioid peptide-degrading enzymes have been known. Accordingly, the effects of the products of the present invention were judged from inhibition rates realized when the products were allowed to act on the opioid peptide-degrading enzyme in the presence of the opioid peptide in vitro.

In the tests, the product of the invention was added to an opioid peptide such as enkephalin or its model compound. After an incubation effected for a given time, the inhibition rates of the product against the opioid peptide-degrading enzyme were examined. Various opioid peptides were used. Generally, high inhibition rates were exhibited as shown in Tables (3) and (4).

TABLE (3)

| | Enzyme Origin Bovine longitudinal muscle Name | | | |
|---|---|---|---|---|
| Principal ingredient (1 μg/1 ml) | Dipeptidyl-carboxy-peptidase | Carboxy-peptidase | Dipeptidyl-amino-peptidase | Amino-peptidase |
| | Substrate | | | |
| | Hip—His—Leu | Hip—L-PheAla | Enkephalin | Enkephalin |
| Compound (1) | 76.4% | — | — | — |
| Compound (2) | 85.0% | 6.2% | — | — |
| Compound (3) | 80.0% | — | — | — |
| Compound (4) | 60% | — | — | 58% |
| Compound (5) | 78.8% | — | + | 88.0% |

TABLE (3)-continued

| | Enzyme Origin Bovine longitudinal muscle Name | | | |
|---|---|---|---|---|
| Principal ingredient | Dipeptidyl-carboxy-peptidase | Carboxy-peptidase | Dipeptidyl-amino-peptidase | Amino-peptidase |
| | | Substrate | | |
| (1 μg/1 ml) | Hip—His—Leu | Hip—L-PheAla | Enkephalin | Enkephalin |
| Compound (6) | 74.2% | 89.8% | + | 97.0% |
| Compound (7) | 76.8% | — | + | — |
| Compound (8) | 78.3% | — | — | — |
| Compound (9) | 68.4% | — | — | — |
| Compound (10) | 73.4% | — | — | — |
| Compound (11) | + | — | + | — |
| Compound (12) | + | — | + | — |
| Compound (13) | + | — | + | — |
| Compound (14) | + | — | + | — |

TABLE (4)

| | Enzyme Origin Monkey brain Name | |
|---|---|---|
| Compound | Dipeptidylaminopeptidase | Aminopeptidase |
| | Substrate Enkephalin | |
| (1) | 98.2% | 87.8% |
| (2) | 97.9% | 87.6% |
| (3) | 97.7% | 85.6% |
| (8) | — | — |
| (9) | — | — |
| (10) | — | — |
| (4) | 62% | — |

Further, to confirm the inhibition effects of the compounds of the present invention, 50% inhibition coefficients (IC$_{50}$) were determined to obtain the results shown in Table (5). The effects of the compounds of the present invention were thus clear.

TABLE (5)

| Principal ingredient | Enzyme/origin | | Substrate | IC50 |
|---|---|---|---|---|
| Compound (2) | dipeptidyl-carboxy-peptidase | bovine longitudinal muscle | Hip—His—L-Lue | 66 μg/ml |
| Compound (2) | angiotensin converting enzyme | rat lung | " | 70 μg/m |
| Compound (2) | Angiotensin converting enzyme | monkey brain | " | 78 μg/ml |
| Compound (5) | amino-peptidase | bovine longitudinal muscle | Enkephalin | 110 μg/ml |
| Compound (6) | amino-peptidase | bovine longitudinal muscle | " | 19 μg/ml |
| Compound (6) | carboxy-peptidase | bovine longitudinal muscle | Hip—L-PheAla | 275 μg/ml |
| Compound (6) | dipeptidyl-carboxy-peptidase | bovine longitudinal muscle | Hip—His—Leu | 100 μg/ml |

The inhibition rate (IC$_{50}$) of the compound of the present invention containing the compound (6) as the principal ingredient on enkephalin (aminopeptidase derived from bovine longitudinal muscle) was as high as 19 μg/ml. This fact suggests that the product can be used as an inhibitor against this enzyme.

The opioid peptide-degrading enzymes derived from bovine longitudinal muscle used in the above examples were purified partially by a process of Goreustein and Snyder S. H., ["Life Sci." 25, 2065 (1979)]. The inhibition effects of the compounds of the present invention on the opioid peptide-degrading enzymes were determined by a process of T. Hazato, M. Shimamura, T. Katayama and T. Yamamoto [B.B.R.C. 105, 470–475 (1982)] (for dipeptidylaminopeptidase), a process of M. Shimamura, T. Hazato and T. Katayama [B.B.A., 756, 223–229 (1983)] (for aminopeptidase) and analogous processes.

(2) The effects of the compounds of the present invention on human bodies were examined.

A human cerebrospinal fluid was dialyzed by using 25 mM of tris-HCl buffer having a pH of 7.0 for 5 hrs. Enkephalin-degrading enzymes contained therein were analyzed according to a radioautography or the like. In the cerebrospinal fluid, the aminopeptidase activity was the strongest. Further, dipeptidylaminopeptidase and dipeptidylcarboxypeptidase activites which were nonselective for bestatin were also recognized.

The compound (3) and (6) of the present invention were allowed to act on the respective enzymes. The compound (3) in a concentration of 2 mg/ml exhibited inhibition effects on all the enzymes. The compound (6) in the same concentraton as that of the compound (3) exhibited inhibition effects on aminopeptidase, dipeptidylcarboxypeptidase and carboxypeptidase.

On the other hand, the aminopeptidase alone was eluted according to the cellulose column chromatography using a NaCl solution as a eluant. IC$_{50}$ values of the above two compounds on the aminopeptidase were determined according to Porapak Q column process and high-performance liquid chromatography using enkephalin as the substrate. The results were compared with those of Arphamenin A and B the inhibitive actions of which on the enkephalin-degrading enzyme have been known. As shown in Table (6), the compounds of the present invention in concentrations lower than those of Arphamenin A and B exhibited the inhibition activities.

TABLE (6)

| Compound | IC50 (μg/m) |
|---|---|
| (3) | 450 |
| (6) | 440 |

TABLE (6)-continued

| Compound | IC50 (μg/m) |
|---|---|
| Arphamenine A | 810 |
| Arphamenine B | 650 |

The external liquid used for the dialysis of the cerebrospinal fluid was examined minutely to reveal that it contained an indogenous inhibitor against the enkephalin-degrading enzymes.

Namely, it is considered that the human cerebrospinal fluid contains both the enkephalin-degrading enzymes and the indogenous inhibitors which inhibit these enzymes and they are well-balanced under normal conditions, a pain being caused when the balance is broken. This fact suggests the usefulness of the compounds of the present invention in vivo.

What is claimed is:

1. A method of inhibiting the action of an opioid peptide-degrading enzyme comprising administering to an organism in need of such treatment an effective opioid peptide-degrading enzyme amount of a compound having the formula:

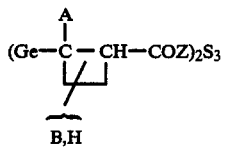

wherein A represents a hydrogen atom, a lower alkyl group or a phenyl group, B represents a hydrogen atom or a lower alkyl group and Z represents a hydroxyl or amino group; wherein said lower alkyl group is selected from the group consisting of methyl, ethyl and propyl.

2. A method as recited in claim 1 wherein A represents a hydrogen atom, B represents a hydrogen atom and Z represents a hydroxyl group.

3. A method as recited in claim 1 wherein A represents a hydrogen atom, B represents a lower alkyl group and Z represents a hydroxyl group.

4. A method as recited in claim 1 wherein A represents a hydrogen atom, B represents a hydrogen atom and Z represents an amino group.

5. A method as recited in claim 1 wherein A represents a hydrogen atom, B represents a lower alkyl group and Z represents an amino group.

6. A method as recited in claim 1 wherein A represents a lower alkyl group, B represents a lower alkyl group and Z represents a hydroxy group.

7. A method as recited in claim 1 wherein A represents a lower alkyl group, B represents a lower alkyl group and Z represents an amino group.

8. A method as recited in claim 1 wherein A represents a phenyl group, B represents a hydrogen atom and Z represents a hydroxy group.

9. A method as recited in claim 1 wherein A represents a phenyl group, B represents a hydrogen atom and Z represents an amino group.

10. A method as recited in claim 1 wherein A represents a phenyl group, B represents a lower alkyl group and Z represents a hydroxy group.

11. A method as recited in claim 1 wherein A represents a phenyl group, B represents a lower alkyl group and Z represents an amino group.

* * * * *

UNITED STATES PATENT AND TRADEMARK OFFICE
CERTIFICATE OF CORRECTION

PATENT NO. : 4,748,187

DATED : May 31, 1988

INVENTOR(S) : Norihiro KAKIMOTO et al

It is certified that error appears in the above-identified patent and that said Letters Patent is hereby corrected as shown below:

Column 1, line 49, where "inactivate" should read --inactivates--; column 2, line 28, where "wherin" should read --wherein--; column 2, line 48, where "a" (second occurrence) should read --an--; column 5, line 12, where "isoloated" should read --isolated--; column 5, line 46, where "poing" should read --point--; column 6, line 9, where "includes" should read --include--; column 6, line 12, where "GlY" should read --Gly--; column 6, line 21, where "inhibit" should read --inhibits--; column 6, line 23, where "(4)" should read --(6)--; column 6, line 43, where "an" should read --a--; column 7, line 33, where "a" should read --an--; column 10, in Table 3 (first column under "Principal Ingredient"), where "(1 µg/1 ml)" should read --(1 mg/1 ml)--; column 11, line 10, in Table 3 (First column under "Principal Ingredient"), where "(1 µg/1 ml)" should read --(1 mg/1 ml)--; column 13, line 2, in Table 6 (second column), where "IC50 (µg/m)" should read --IC50 (µg/ml)--; column 13, line 9, where "indogenous" should read --endogenous--; column 13, line 13, where "indogenous" should read --endogenous--; and column 13, line 15, where "a pain" should read --pain--.

Signed and Sealed this

Twenty-seventh Day of March, 1990

Attest:

JEFFREY M. SAMUELS

*Attesting Officer*   *Acting Commissioner of Patents and Trademarks*